US006824984B1

(12) United States Patent
Rastogi et al.

(10) Patent No.: US 6,824,984 B1
(45) Date of Patent: Nov. 30, 2004

(54) NUCLEOTIDE SEQUENCES FOR DETECTION OF BACILLUS ANTHRACIS

(75) Inventors: Vipin K. Rastogi, Bel Air, MD (US); Tu-Chen Cheng, Timonium, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/241,383

(22) Filed: Sep. 9, 2002

Related U.S. Application Data

(62) Division of application No. 09/879,027, filed on Jun. 12, 2001, now Pat. No. 6,448,016.

(51) Int. Cl.[7] ........................ C12Q 1/68; C12P 19/34; C07H 21/02; C07H 21/04
(52) U.S. Cl. ........................ 435/6; 435/91.2; 536/23.1; 536/24.31; 536/24.32; 536/237
(58) Field of Search ................... 435/6, 91.2; 536/23.1, 536/24.32, 24.33, 23.7

(56) References Cited

U.S. PATENT DOCUMENTS

| | | | | |
|---|---|---|---|---|
| 6,087,104 | A | | 7/2000 | Yamada et al. ................. 435/6 |
| 6,255,476 | B1 | * | 7/2001 | Vinayak et al. .......... 536/25.32 |
| 6,582,908 | B2 | * | 6/2003 | Fodor et al. .................... 435/6 |

OTHER PUBLICATIONS

Stratagene Catalog. 1988, p. 39.*
Patra et al. FEMS Immunology and Medical Microbiology. 1996. 15: 223–231.*
Hutson et al. Journal of Applied Bacteriology. 1993. 75: 463–472.*
Jackson, P., et al, "PCR Analysis of Tissue Samples from the 1979 Sverdlovsk Anthrax Victims: The Presence of Multiple *Bacillus Anthracts* Strains in Different Victims" Microbiology, vol. 95, pp. 1224–1229, Feb. 1998.
Andersen, G., et al, "Identification of a Region of Genetic Variability Among Bacillus Anthracis Strains and Related Species" Journal of Bacteriology, Jan. 1996, vol. 178, No. 2, pp. 377–384.
Patra, G., et al., "Isolation of a Specific Chromosomic DNA Sequence of Bacillus Anthracis and Its Possible Use in Diagnosis", FEMS Immunology and Mical Microbiology 15 (1996) pp. 223–231.
Williams, JG, et al, "DNA Polymorphisms Amplified by Arbitrary Primers are useful as Genetic Markers", (Abstract Only), Nucleic Acids Research, vol. 18, Issue 22, pp. 6531–6535.

* cited by examiner

Primary Examiner—Carla J. Myers
(74) Attorney, Agent, or Firm—Ulysses John Biffoni

(57) ABSTRACT

The invention provides purified and isolated DNA fragments from *Bacillus anthracis* chromosomal DNA, primer sets and probes derived therefrom, as well as kits and detection methods for *B. anthracis*. The methods of the invention provide for specific detection of anthrax over closely related strains of *Bacillus*, as well as accurate detection of low numbers of *B. anthracis* in an environmental sample containing large amounts of non-specific DNA. The invention is applicable to food, health care, and military applications.

16 Claims, 10 Drawing Sheets

280FR

```
GCCTACGACTCACTATAGGGCGAATTGGGCCCTCTAGATGCATGCTCGAGCGGCCGCCAG    60
TGTGATGGATATCTGCAGAATTCGGCTTATCAAGCTGCTCTACTAAATATTGGAGAGCTT   120
CGTCAGACAACCTTACACCTTCGTATATGCTTCTAATTCTGCCTTCGATTCCTCTCTG     180
TAATTCACTAATTTCTATTTGTTTCCCAAACATATTGGTTTATATGGAAAATGAT        240
TTTGCATCGTCACCGCATGAATAAATGTAGGTTGTTTCTCTTTTTAATTCATCTATTA     300
TTTCTTTACTCATAGATAAATCACCGATATTATCTCCAACTACTCTTTGTTTTTCATCG    360
TATCTTCTGCATTAAAATTATCGAATCCTAAATGTTTATATACATCTTCCCGTTTATAAA   420
ACGATCGGTTAAAAGCATGGATTGCACTTGCATATAATCCTTGTTCTTTAATTCACTTG    480
CAACTGATGGGATTTCTTCTGAGTAACTCGTTAATGCTTCAAATTCTCTGTTTGCTGTATCCCTC 540
TTAAAAGACTCATTGAGTAAGCTATCGTTTGTCCCCCTGGGAAATTCTCTGTATAACGATGTAAATTCG 600
CAAATGTAGGAGCTATCGTTTGTCCCCCTGGGAAATTCTCTGTATAACGATGTAAATTCG   660
GCACTGGATCTTCGCTAAATGAAAGATTCGTTAGTTTTGTCGGATCCCAAGAAGCTTCAC   720
TCATAATAATATAATATTTGGCTTCTCTACTTTTGTTGTGCCTTTACTTTACCGCTAT     780
ATTGTTTTCTATATCCTTGCAATTTGCTGCATATTTCTTTGAATATCCCTCTGCT        840
CTTTAATAACTGTCGTATCTAAGTTACTTAAAATCCAATAATAAAACCATTCGCTTTAT    900
AATTTGCAGCTTGATAAGCCGAATTCCAGCACACTGGGCCGTTACTAGGGATCCGAGC     960
TCGGTACCTAGCAAGGGTATCAAAG-3'                                    985
```

FIG. 1a

173F
GGCGAATTGGGCCCCTCTAGATGCATGCTCGAGCGGCCGCCAGTGTGATGGATATCTGCAG    60
AATTCGGGCTTCAGGCGGCGTTGGAGCAGGCTTTGTGAACATTATTATGTATGCGATTATC   120
GCAGTCTTTATATCTGGATTAATGGTCGGACGGACACCAGAGTTTTTAGGTAAGAAAATT   180
GAAGGTAAGGAAATGAAATTAATTGCGGTAACGATACTATTTCATCCATTGCTCATTTA    240
GGATTTTCGGCATTAGCTCTTTCAACAAGTTTAGGGACGGATGCTATTTCTCATTCCGGT    300
TTCCACGGTTTAACGCAAGTTGTATATGAATATACATCGTCAGCTGCGAATAACGGATCT    360
GGATTTGAAGGATTAGGAGATAATACACCGTTTGGAATATTACGACTGGTTTAGTTATG    420
TTTTTAGGACGCTACTTCAGTTTAATTACGATGCTAGCGTTGTGGCAGCTTCGCTAAAGAG    480
AAAACGGTTGTACCAGAGAAACAGTTGGAACGTTCCGGACAGATAATGGTTTATTGGAGGC    540
ATCTTTATTGGACGATTGTAATTGTGTGCCGTTAGCATTCTTCCCAATGTTAGTACT     600
CGGACCAATTGCAGAATTTCTTACATTGAAGTAATGGAGGGTAAATGATGAGACCGGTAG    660
TAGTAAAGAAAAAAGAGTTAATGAGTCACACATACACATGCCGTAGAAGA-3'       711

GACTCCTATAGGGCGAATTGGGCCCTCTAGATGCATGCTCGAGCGGCCGCCAGTGTGATG 60
GATATCTGCAGAATTCGGCCGCGAGCACTCTATAAAGCACAACAATGGGTTGATACTCAC 120
AGTCCAGAAGAGATTGCTGATGCCGTTCTCCGTTATTTAAAGACACTTCAAAAGACATT 180
ACAGAAAAAGTAATTGAACGGTATAAAAAGCAACATTCTTATGCAGACAAATCCGCTATTA 240
GATGCTGAAGAATGGAAACAGCTCCAAACGATTATGAAAGAAGCTGGCGAATTACAAAAA 300
GAAGTTCCACATGAAGCGCTCGTCAATACAAAAATTGCCGAGAGCGTTATTAAGAAATAG 360
AGGCGAAGTGTATGAGCTTTTACAAATACGTAACGTTTCTCACTGCTTTTCGCAAAAG 420
AGAATGCCAAGCTGATTCTCGAAATATGAGTTTACAAGTGGAAGAGGCGAATTCATT 480
CTATACTTGGTCCAAGTTGCGGCAAAACGACACTCCTCCATTATTGCCGGCTGC 540
TTGATCCAATTGAAGGTATCGTCTTTTAGATGGTGAGCCATTACAACGAAAACTTCAT 600
CTATGGGTATATGTTGCAGCAAGGACTACTTGTTTCCTTGAAGACAATTGAAGAAAAT 660
ATTATGCTCGGACTTCATATCCGAAAAATTTACGATGAACAGAGACGAAAGAACATACTTTA 720
CA-3' 722

```
CTAGGTACCGAGCTCGGATCCCTAGTAACGGGCCGCCAGTGTGCTGGAATTCGGCTTCAGG    60
CGGGTCACAACGATTAAGAAAATAAGAGTTAAGCTCGTTAATACTGTATTTAAAGC        120
AATCTCATTCGGTGTTTTTGACGAGCAGCTCCTTCTACTAACGAAATCATTTATCAAT      180
AAAGGATTACCAGGATTACTCGTAATGACAATCGTAATCTCATTCACTTACAACCATCGT   240
ACCGCCTGTTACGGAACAAAATCACCGCCCGCTTCTTTATTACAGGTGCTGATTCCCC     300
TGTAATCGCAGATTCATCAACAGACGCTAATCCTTAATGACTTCACCATCACTGGAAT    360
CATCTCACCTTGCTTTACAATAACAACGTCATCTTTTTTAAGGTCAGTTGCTGAAACTTG   420
AACAATTTCTCCATTTCTTTACAACACATTGCAAACACATCTTTCTCGACTGCTTTAA    480
AGAATCAGCTTGCGCTTACCACGACCTTCTGCTAATGCTTCTGCAAAGTTCGCAAATAA    540
AACTGTAAATAATAGAATGAGAGAAACAGTTATATTAAACCATCCTGGTATACTACTAGA  600
ATGACTTGGAAGAAACGATAAAATGAACGTAATGAACCAATTTCTACAACGAACAT      660
AATCGGATTCTTTATCATAACTTTCGGATTCAATTTCGCAACGGATTGTTTCATCGCATG   720
TTTCACGATATCACGATCCATCGTTTTCGCTTGG-3'                           754
```

```
CTACGACTCCTATAGGGCGAATTGGGCCCTCTAGATGCATGCTCGAGCGGCCGCCAGTGT     60
GATGGATATCTGCAGAATTCGGCTTGAGTAAGCGGTATGATAAATGTATAACAACTAGAA    120
AGGAGTGGTAAAACAAATGTCACTAGAAGCGCTCATTATTTTCTTGCTAAATGCGG        180
GTCAGCTTGCAGAGAATTCGAAGGTGGATGTACATAAAGAGCAGAAGATGCTTATGTAT    240
ATGTTCAGAAAGAGAGAAATAAACTTTATTTATATAAACGAAAAAGCCAATCC           300
ACAGGATTGGCTTTTTGTCATTAACGAGAGTAGAACTCTACGATTAATGCTTCGTTGATT    360
TCAGCTGGTAACTCAGCGCGCTCAGTACGAGTGTAAGTAGCTTCTAATTTGTCAGCA       420
TCGAAAGTTAAGTATTCTGTACGAAGTTGTTAACTTCGATCGCTCTTAACAACAACA       480
AGGTTGTTAGATTTTCGCGAACGCTGATAGTTTGACCAGGTTTACACGGTAAGATGGG      540
ATATCTACGCGAGCACCATCAACCATGATGTGTTATTACTAATGGGCGAGCTGCA         600
CGACGAGTGGGAGGTAAGCCCATACGGTAAACTAAGTGTCAAGAGCTTCAAGAAGG        660
ATCATGAAGTTTCGCCGTGCTGCTTACCAGGCATTTACCTGCTGGTCAAATGTGCGACGG   720
AATTGACGCTCAGTCATGCGACGAAGTTTTGTTCTGTAATGTAAA                   780
CCGTATTCTGAAATTCTTTCCGTGCCGCTTACTCAAGCCGTAAGGGCGT               840
TTTCTAATTCTTTCCGTGCCGCTTACTCAAGCCGAATTCCAGCACACTGGCGGCCGT       900
TACTAGTGGATCCGAGCTCGGTACCAAGCAGG-3'                             932
```

FIG. 1e

280FR(LEFT & RIGHT FLANKING REGIONS)

```
GCCTACGACTCACTATAGGGCGAATTGGGCCCTCTAGATGCATGCTCGAGCGGCCGCCAG     60
TGTGATGGATATCTGCAGAATTCGGCTTATCAAGCTGCTCTACTAAATATTGGAGAGCTT    120
CGTCAGACAACCTTACACCTTCGTATATGCTTCTAATTCTGCCTTGATTCCTTCTG        180
TAATTCACTAATTTCTATTTGTTTCCCAAACATATTGGTTTATATGGAAAATGAT         240
TTTGCATCGTCACCGGCATGAATAAATGTAGGTTGTTTCTCTTTTTAATTCATCTATTA    300
TTTCTTTACTCATAGATAAATCACCGATATATCTCCAACTACTTCTTTGTTTTTCATCG    360
TATCTTCTGCATTAAAATTATCGAATCCTAAGTGTTTATATACATCTCCCGTTTATAAA    420
ACGATCGGTTAAAAGCATGG...                                        440
                    ...CAC                                     720
TCATAATAAATATATATTGGCTTCTCTACTTTGTTGTGCCTTACTTTACCGCTAT         780
ATTGTTTTCTATATCCCTTTGCAATTTTCTGTGCATATTTCTTTGAATATCCCTGGCT     840
CTTTAATAACTGTCGTATCTAAGTTACTTAAAAATCCAATAATAAAACCATTCGCTTTAT    900
AATTTGCAGCTGATAAGCCGAATTCCAGCACACTGGGCGCCGTTACTAGGATCCGAGC     960
TCGGTACCTAGCAAGGGTATCAAAG-3'                                   985
```

FIG. 1f

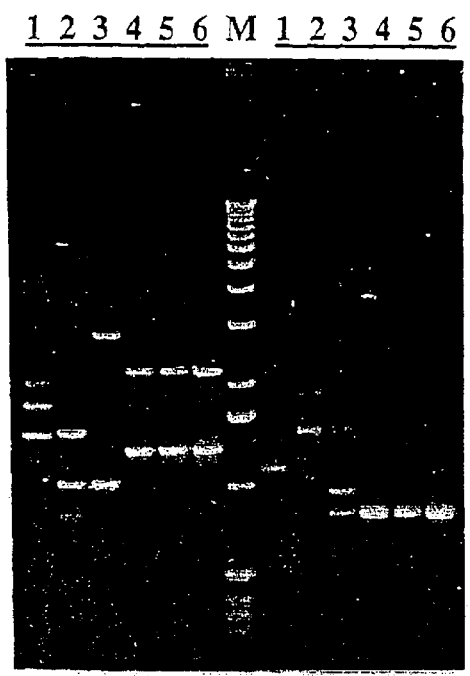 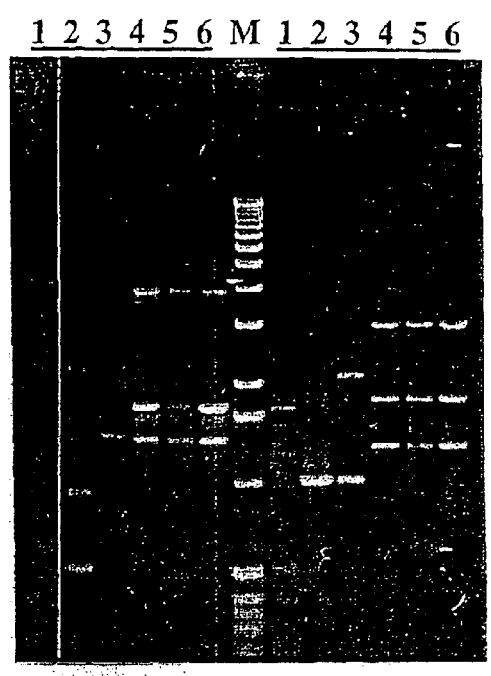
Figure 2a
Figure 2b

Primer 173    Primer 115    Primer 361

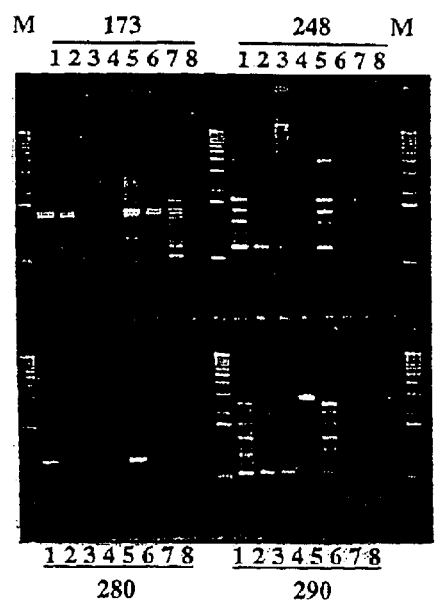
Figure 4
Figure 5
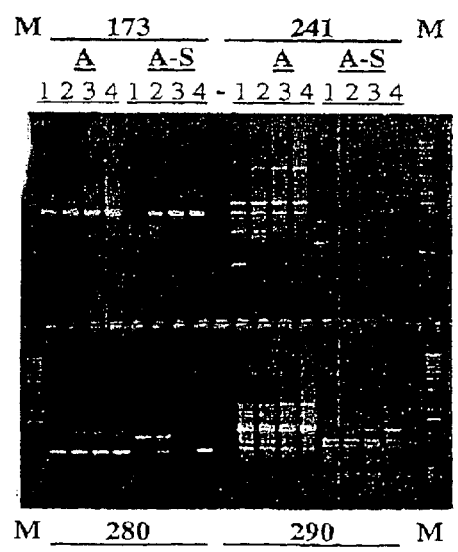

NUCLEOTIDE SEQUENCES FOR DETECTION OF BACILLUS ANTHRACIS

This application is a division of application Ser. No. 09/879,027, filed Jun. 12, 2001, now U.S. Pat. No. 6,448,016.

GOVERNMENTAL INTEREST

The invention described herein may be manufactured, used, and licensed by or for the U.S. Government.

FIELD OF THE INVENTION

The present invention relates generally to the detection of *Bacillus anthracis*. More specifically, the invention relates to anthrax-specific polymorphic signature sequences identified on, and isolated from the anthrax chromosome DNA for use as *B. anthracis*-specific markers. Primer sets and hybridization probes designed from these DNA fragment sequences, as well as amplification of the fragments, can be used in a variety of platforms for anthrax detection.

BACKGROUND OF THE INVENTION

Anthrax—primarily a disease of herbivorous animals but of rare occurrence in humans—is caused by *Bacillus anthracis*. Cutaneous anthrax is acquired via injured skin or membranes, entry sites where the spore germinate into vegetative cells. Proliferation of vegetative cells results in gelatinous edema. Alternatively, inhalation of the spores results in high fever and chest pain. Both types can be fatal unless the invasive aspect of the infection can be intercepted. *Bacillus anthracis* is a biological warfare (BW) agent. Ten grams of anthrax spore can kill as many people as a ton of the chemical warfare agent, sarin. Due to the highly lethal nature of anthrax and BW agents in general, there is great need for the development of sensitive and rapid BW agent detection. Current detection technology for biological warfare agents have traditionally relied on time-consuming laboratory analysis or onset of illness among people exposed to the BW agent.

In theory, the use of specific antibodies or distinguishing DNA probes are the two approaches to modernizing detection technology in this field. However, antibody-based detection of threat agents suffers from drawbacks. For example, interference from other environmental contaminants precludes detection, or detection limits of current levels fail to meet the detection thresholds set by governmental testing protocols. Alternatively, the threat agent, such as with anthrax spore, may be poorly immunogenic.

Since a sample suspected of containing a BW agent like *B. anthracis* could contain such a small yet lethal amount of spores, and an overwhelming amount of other interfering materials, the ability to amplify the agent's genomic material affords a choice of target sites for developing signature probes for specific detection of that agent. Development of highly discriminating techniques are crucial to achieving the stated goals of rapid and sensitive BW detection.

Current PCR-based detection methods of *B. anthracis* rely on the use of primers amplifying tripartite exotoxin genes and/or the polyglutamic capsule genes (Jackson et al, Proc. Natl. Acad. Sci, 95: 1224–9 (1998)). Both sets of genes comprise virulence factors and are located on the two indigenous plasmids of anthrax bacteria, pXO1 (174 kbp; toxin) and pXO2 (95 kbp; capsule). Under normal conditions, the two plasmids in *B. anthracis* do not move across the related bacilli of the "*B. cereus* group" (which is comprised of *B. anthracis, B. cereus, B. thuringiensis* and *B. mycoides* (although *B. mycoides* does not produce toxin and therefore may be grouped differently from the other three members)). However, under certain conditions, these plasmids are known to be transferred from *B. anthracis* to *B. cereus* and *B. thuringiensis* (Ruhfel et al, J. Bact., 157: 708–11 (1984)). Yet *B. cereus* and *B. thuringiensis* containing one or both of these plasmids do not cause anthrax. Therefore, detection of anthrax based solely on virulence factors can give rise to a false-positive determination.

Two chromosomal DNA fragment sequences from *B. anthracis* have been previously identified and used in identifying the presence of *B. anthracis* bacteria. One, designated Ba813, is a 277 bp long DNA fragment (Patra et al., FEMS Microbiol. 15: 223–231 (1996)) and the other, vrrA, is a region of sequence variability containing variable repeats (caa tat caa caa) (Anderson et al., *J. Bacteriol. 178: 377–384* (1996)).

Additionally, Yarnada et al (U.S. Pat. No. 6,087,104) identified unique regions of the DNA gyrase sub-unit B (gyrB) gene for each of the closely related bacteria of the *B. cereus* group, and designed oligonucleotide primers corresponding to those unique regions for amplification-based detection methods. However, amplification of DNA segments unique to each of the *B. cereus* group members occurred only when the correct target strain DNA by itself was present in the PCR protocol.

However, since the development of more rapid and more sensitive BW detection methodologies is of such importance to the military as well as public health sectors of the U.S. government, there is great need to continue the process of identifying, cloning, and sequencing of polymorphic DNA markers from chromosomal DNA of threat agents. With this purpose in mind, comprehensive libraries of BW agent-specific signature sequences can be built, and from there useful diagnostic primers and probes can be designed for highly discriminating detection methods. The present invention as herein described fulfills these objectives.

SUMMARY OF THE INVENTION

Accordingly, it is an embodiment of the invention to provide purified and isolated DNA sequences from the chromosomal DNA of *B. anthracis*, as shown in FIGS. 1a–1f and corresponding to SEQ ID NOS: 1–7.

Another embodiment of the invention is the use of these sequences in diagnostic assays to accurately analyze samples for environmental contamination by *B. anthracis* spores and for the early diagnosis of anthrax in human and non-human animals. In this embodiment resides the capability not only to distinguish over closely related Bacillus species, thereby affording more sensitive and reliable detection for anthrax, but also to detect a very minuscule concentration of anthrax spores in the presence of an overwhelming amount of unrelated non-specific environmental DNA.

In yet another embodiment, the invention provides for primer pairs (SEQ ID NOS: 8–15) designed from the aforementioned purified and isolated DNA sequences of the first embodiment. The primer pairs are useful in carrying out PCR amplification-based detection of *B. anthracis*. Alternatively, the invention further provides hybridization probes designed from the novel isolated DNA sequences of the first embodiment, such probes being useful in a number of assay platforms for *B. anthracis*.

Kits useful in the practice of the invention are also provided, containing at least one container comprising at least one pair of primers or at least one hybridization probe specifically designed to selectively amplify or bind, respectively, chromosomal DNA of *B. anthracis*.

These and other embodiments of the invention will be better appreciated by the following detailed disclosure.

BRIEF DESCRIPTION OF THE FIGURES

FIG. 1*a* depicts one of the subject chromosomal DNA fragments (985 bp) isolated from *B. anthracis* and referred to as 280FR (SEQ ID NO: 1).

FIG. 1*b* depicts one of the subject chromosomal DNA fragments (711 bp) isolated from *B. anthracis* and referred to as 173F (SEQ ID NO: 2).

FIG. 1*c* depicts one of the subject chromosomal DNA fragments (722 bp) isolated from *B. anthracis* and referred to as 290BF (SEQ ID NO: 3).

FIG. 1*d* depicts one of the subject chromosomal DNA fragments (754 bp) isolated from *B. anthracis* and referred to as 173R (SEQ ID NO: 4).

FIG. 1*e* depicts one of the subject chromosomal DNA fragments (932 bp) isolated from *B. anthracis* and referred to as 248FR (SEQ ID NO: 5).

FIG. 1*f* depicts the left (bp 1–440) (SEQ ID NO: 6) and right(bp 718–985) (SEQ ID NO: 7) fling regions of the chromosomal DNA fragment referred to as 280FR (FIG. 1*a*), which flanking regions are adjacent to a previously identified *B. anthracis* fragment Ba8(3.

FIGS. 2*a*, 2*b*, 3*a*, and 3*b* collectively depict developed electrophoretic gels of the RAPD amplification profile using random primers and genomic DNA isolated from: 1) *Agrobacterium tumifaciens;* 2) *Bacillus thurigiensis;* 3) *B. cereus;* 4) *B. anthracis* Δ Sterne (pOX1–/pOX2–); 5) *B. anthracis* Δ Ames (pOX1–/pOX2+); and 6) *B. anthracis* Ames (wild-type, pOX1+/pOX2+). Primers are indicated below the gel.

FIG. 4 depicts the developed electrophoretic gel of the RAPD amplification profile using random primers of anthrax-specific DNA in the presence of different amounts of non-specific environmental sludge DNA.

FIG. 5 depicts the developed electrophoretic gel showing the detection limit of anthrax-specific DNA probes in spiked environmental samples containing from 0.001–1.0 ng of anthrax DNA.

DETAILED DESCRIPTION OF THE INVENTION

Figure 3A:
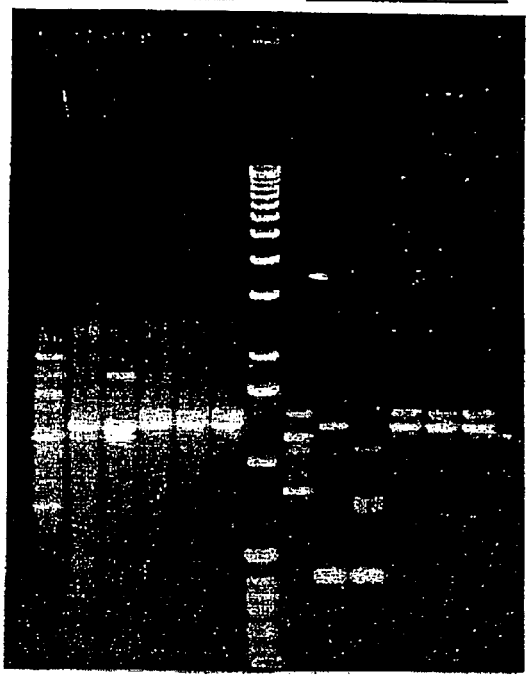
Figure 3B:
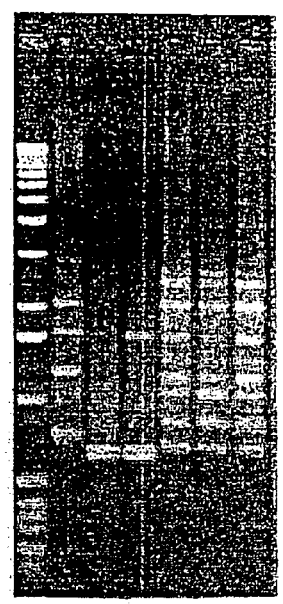
Figure 6:
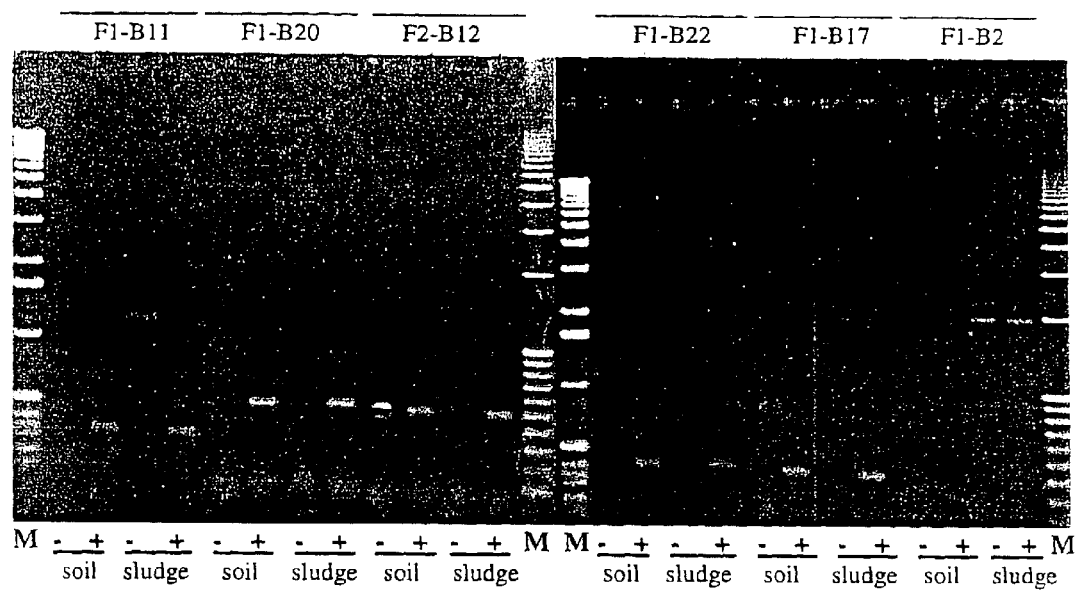
FIG. 6 depicts the results of amplification of anthrax-specific DNA from spiked soil/sludge sample using the high-fidelity primer sets according to the invention.

The process of identifying genus-specific signature sequences or polymorphic loci can be approached in a number of ways. One approach entails the cloning of genomic material from, e.g., related bacteria, followed by laboriously eliminating the common shared regions among the related organisms. Such an approach was utilized by Patra et al in identifying anthrax chromosome fragment, Ba813.(FEMS Microbiol. 15: 223–231 (1996)). Alternatively, the process of identifying polymorphic loci and the development of diagnostic probes or primers can be greatly simplified by using RAPD (randomly amplified polymorphic DNA), a PCR-based technology (Williams et al, Nucleic Acids Research, 18(22): 6531–35 (1994)). In this technique, small amounts of DNA are subjected to PCR using a single oligonucleotide of random sequence as a primer. The amplification products are resolved on agarose or polyacrylamide gels giving rise to a pattern that is strain specific. Many of the products generated by RAPD-PCR are derived from repetitive DNA sequences. As these sequences are frequently species-specific, RAPD-PCR is potentially a quick method for developing species-specific diagnostic PCR primers and probes.

Accordingly, in the present invention, random sequence primers of, e.g., 10 nucleotide bases (ten-mers), are used under low-stringency annealing temperatures with genomic DNA from a given BW agent such as *B. anthracis* and its close relatives in PCR protocols. The number and size of amplified fragments derived from genomic DNA of a desired BW agent under these conditions depend on the existing number of priming sites and the distance between the priming sites in opposite direction on the two strands of DNA. In practice, the number and size of amplified fragments depend on the ability of a single primer to anneal to complementary sites on the two strands in opposite directions (5'→3' and 3'→5') within ~2500 bp of each other. Identification, cloning, and obtaining of sequence information from polymorphic DNA markers located on the chromosomal DNA enables the formation of a library of agent-specific signature sequences, also referred to as a DAF pattern (DNA Amplification Fingerprinting pattern). As between the closely-related members of a group such as *B. cereus* RAPD produces a common sub-set of amplified DNA fragments since the genomes are largely similar. However, there will be a further sub-set of amplified fragments unique to each individual member on account of inherent DNA polymorphisms.

A general outline and brief description of the methods utilized in the present invention in order to elucidate polymorphic DNA markers from the chromosomal DNA of *B. anthracis* follows. A more detailed description is provided in the "Examples" section.

The Isolation and Screening of DNA From Anthrax and Related Bacteria Against Random Primers in PCR Protocols DNA from wild-type *B. anthracis* strain Sterne, and DNA from two plasmid-free strains of *B. anthracis*, and a strain containing only the pXO2 plasmid were prepared following standard procedures known to one of ordinary skill for isolation of genomic DNA. The DNA's were diluted to a concentration of 1 ng/ml, and the majority of DNA was in the size range of about 30–50 kbp. As a control, DNA from other related bacilli, *B. cereus, B. thuringiensis* and *B. subtilis* were also prepared in like manner and included. For initial screening purposes only, DNA from a unrelated bacterium, *Agrobacterium tumifaciens*, was also included.

Three hundred (300) random decamer (10-mer) primers were purchased from a commercial source (University of British Columbia, Vancouver, BC, Canada). RAPD-PCR amplification reactions were conducted in routine manner on the DNA of the several strains *B. anthracis* and on the DNA of the related bacilli.

The Analysis of PCR Amplified DNA Through Agarose Gel Electrophoresis

The PCR amplified DNA was analyzed through agarose gel electrophoresis and the DAF pattern was photographed and documented. Primers that amplified unique-size DNA fragments from wild-type anthrax strain and plasmid-free strain were identified. After several rounds of amplification, primers amplifying consistent DNA fragments from anthrax DNA were selected.

Fragment Amplification at the Preparatory Level

The fragments identified in the preceding step were amplified at a preparatory level and purified following gel electrophoresis. Five DNA fragments were then cloned in pTA cloning vector (from Invitrogen Co., CA) for sequencing.

Nucleotide Sequencing and Computer Analysis

The nucleotide sequence for each of the five cloned DNA fragments was determined following the manufacturer's protocol based on the well-known dideoxy sequencing method of Sanger et al (*Proc. Natl. Acad Sci,* 74: 5463–67 (1977)) using an automated dideoxy sequencer (Perkin-Elmer, Applied Biosystems Division, Foster City, Calif.). Computer analysis of each of the DNA sequences was performed using MacVector, version 6.0 (Oxford Molecular Ltd., Oxford).

The five DNA fragment sequences from anthrax chromosome are 280FR (FIG. 1A) (SEQ ID NO: 1), 173F (FIG. 1B) (SEQ ID NO: 2), 290BF (FIG. 1C) (SEQ ID NO: 3), 173R (FIG. 1D) (SEQ ID NO: 4), and 248FR (FIG. 1E) (SEQ ID NO: 5). The sequences represented by SEQ ID NO: 2 through SEQ ID NO: 5 did not match any known sequence in the Genebank database. A region of 277-bp in sequence 280FR (SEQ ID NO: 1), from bp 441 to bp 717 was found to be homologous to Ba813, an anthrax-specific chromosomal region identified by Patra et al., supra. Accordingly, it is not an embodiment of the present invention to seek protection for the 277-bp region of 280FR by itself. Nor is it an embodiment of the invention to seek protection of any primer or probe derived or designed exclusively from within bp 441 to bp 717, inclusive. However, the sequences of each of the two regions ((FIG. 1F) bp 1- bp 440 (SEQ ID NO: 6) and bp 718 bp 985 (SEQ ID NO: 7)) that flank the 277-bp region were not found to match any known sequence in the Genebank database. Accordingly, it is intended that the flanking regions represented by SEQ ID NO: 6–7 are part of the protection sought herein. Consequently, any primers and probes derived in whole or in part (i.e., primers and probes derived from the juncture of 5' or 3' end of Ba813 with either flanking region) from these regions are also contemplated.

As will become evident in the examples set forth hereinbelow, the five DNA fragment sequences of the invention (SEQ ID NO: 1–5) are unique in their ability to discern between anthrax DNA and the DNA of the remaining members of the *B. cereus* family. Hence the five sequences provide a novel "blueprint" for design of numerous primer pairs and hybridization probes useful for diagnostic applications.

Primers

A number of primer sequences were designed from the cloned 280FR, 173F, 290BF, 173R, and 248FR DNA sequences. These primer sequences are generally from 10 to 30 bases in length, more preferably, from 15 to 20 bases in length. The primers were designed using MacVector, version 6.0 (Oxford Molecular Ltd., Oxford) and primer synthesis was carried out by Life Technologies, Inc. (Gaithersburg, Md.). Primers were designed to amplify fragments of *B. anthracis* chromosomal DNA in the size range of from about 130 to 550 base pairs, preferably from 300 to 500. A representative number of primers according to the invention are as follows:

| Primers | Ref. Name | |
|---|---|---|
| 5'-CAT TCG GTG TTT TTT GAC GAG C-3' | R173F1 | (SEQ ID NO: 8) |
| 5'-CTT TGC AGA AGC ATT AGC AGA AGG-3' | R173B22 | (SEQ ID NO: 9) |
| 5'-TGT TCC AAG AAT GAA GCG TAC TCC-3' | R290F1 | (SEQ ID NO: 10) |
| 5'-TGA AGC CTA CTC CCG TTT CAA G-3' | R290F4 | (SEQ ID NO: 11) |
| 5'-TCA CCG TTA GAA TCA CGC CAC C-3' | R290B11 | (SEQ ID NO: 12) |
| 5'-GCC AAA ACA TTT ATC GTC CCAG-3' | R290B17 | (SEQ ID NO: 13) |
| 5'-CAA TGG GTT GAT ACT CAC AGT CCA G-3' | F290F1 | (SEQ ID NO: 14) |
| 5'-CCT TGC TGC AAC ATA TAC CCC ATA G-3' | F290B20 | (SEQ ID NO: 15) |

The above primers were paired as a forward and reverse primer set to give the following expected fragment size during amplification:

| Primer Combination | Expected Fragment Size (base-pair) |
|---|---|
| R173F1 & R173B22 (SEQ ID NO: 8 & 9) | 390 |
| R290F1 & R290B11 (SEQ ID NO: 10 & 12) | 330 |
| R290F4 & R290B17 (SEQ ID NO: 11 & 13) | 360 |
| F290F1 & F290B20 (SEQ ID NO: 14 & 15) | 520 |

Primers according to the invention may optionally have a detectable label or tag conjugated thereto. Suitable labels or tags are well-known to those working in the field, and, for example, may be chosen to provide a radioactive, calorimetric, fluorometric or luminescent signal depending on the particular application. Incorporation of an appropriate visualization label into custom-synthesized primers and probes follows routine protocol of the DNA synthesizer employed. It is within the preferred scope of the invention, for example, that the primers herein described be synthesized to incorporate a fluorescent tag so that detection of anthrax organism can be carried out on a Taq-man® platform or other suitable diagnostic medium.

Gene Probe Approach

Unique fragments selected from the five *B. anthracis* chromosomal DNA fragments shown in SEQ ID NO: 1–5 can be synthesized in large quantities through polymerase chain reaction, and conjugated to any solid support, e.g., glass or silica beads, multiwell plate, dipstick, or the like. The conjugated fragments are rendered single-stranded according to well-known chemical treatment and are used as hybridization probes for detecting anthrax in an environmental sample suspected of contamination.

Alternatively, probes consisting of much smaller DNA fragments can be prepared from amplification products obtained using the primer sets or pairs described above. The fragments of this embodiment are from approximately 100 to 500 bp in length, and more preferably from 170 to 350 bp. A probe designed to detect amplified products of anthrax chromosomal DNA sequence is preferably designed not to hybridize to the sequence of the primers used for amplification. In such an application, it is preferable that the probe be designed to detect amplification products by hybridizing to sequences between the primer sequences.

In the practice of anthrax detection methods using the probes of the invention, at least one signature probe hybridizing with specificity to amplified anthrax chromosomal DNA is detectably labeled. For example, at least one probe is labeled with a biotin moiety and/or at least one probe labeled with a fluorescently labeled probe. The amplified DNA fragments are then bound to a solid support such as a bead, multiwell plate, dipstick, or the like that is coated with streptavidin. The presence of bound amplified DNA fragments can be detected using an antibody with fluorescent tag conjugated to alkaline phosphatase or horseradish peroxidase. The enzymatic activity of alkaline phosphatase or horseradish peroxidase can be detected with a colored, luminescent or fluorimetric substrate, or conversion of the substrate (such as pNPP for alkaline phosphatase) to product can also be used to detect and/or measure the presence of B. anthracis PCR products.

The amplification-based method for detection of B. anthracis in a sample comprises selecting at least one pair of primers derived from the nucleotide sequences represented by SEQ ID NO: 1–7, which primer pair(s) is/are specific for B. anthracis DNA but not which does not recognize, or anneal to DNA from the related strains B. cereus, B. thuringiensis, and B. subtilis. The primers are then mixed with a sample containing non-specific DNA and suspected of containing DNA from B. anthracis. Using standard PCR, amplification is carried out on any DNA to which the primers in the previous step have annealed. If any amplification product is formed it is subjected to analysis by separation and detected using suitable detection means. As mentioned supra, the primers used in the present amplification-based methods are not derived exclusively from within the region of bases-pairs spanning 441 to 717, inclusive, of SEQ ID NO: 1. Moreover, the same proviso applies to any probe derived from SEQ ID NO: 1.

A further embodiment of the present anthrax detection methods is aimed at increasing the specificity for recognition of B. anthracis to the exclusion of other related strains of the B. cereus family, thereby reducing the likelihood of false positive indications. As discussed supra, the plasmids of B. anthracis, which carry the virulence factors TOX gene and CAP gene, can transfer under certain conditions to the other related members of the family. Although present in these related strains, the virulence factors do not cause anthrax infection. Accordingly detection methods for anthrax based on virulence factors alone are not adequate. Hence, by employing one or more primer pairs or one or more hybridization probes of the invention in conjunction with primers specifically amplifying TOX gene and CAP gene of B. anthracis in detection protocols, the likelihood of false positive indications is reduced. Thus, a true positive indication for anthrax would require not only detectable amplification products of TOX and CAP genes, but also, and more dispositively, detectable amplification product from B. anthracis chromosomal DNA.

The present invention lends itself readily to the preparation of "kits" containing the elements necessary to carry out detection methods for B. anthracis. Such a kit may comprise a carrier being compartmentalized to receive in close confinement therein one or more container, such as tubes or vials. One of the containers may contain unlabeled or detectably labeled DNA primer pairs or one or more hybridization probe(s). The labeled DNA primers may be present in lyophilized form or in an appropriate buffer as necessary. One or more containers may contain one or more enzymes or reagents to be utilized in PCR reactions. These enzymes may be present by themselves or in mixtures, in lyophilized form in appropriate buffers.

In an alternate embodiment, the kit would contain at least one container of optionally detectably labeled primers or probes according to the invention, and at least one container with e.g., a primer pair specifically amplifying or a hybridization probe for TOX gene and CAP gene of B. anthracis.

Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies and the like.

EXAMPLES

The following examples are intended solely to illustrate one or more preferred aspects of the invention and are not to be construed as limiting the scope of the invention.

Materials and Methods

Soil and Sludge Source:

Activated sludge was obtained from Back River water treatment plant in Dundalk, Md., and used for isolation of genetic material. The soil samples were collected from farm area around Harford county, MD, and US Army APG, Edgewood Arsenal, Edgewood, Md.

Anthrax DNA and Random Primer Source:

DNA from wild-type B. anthracis strain Sterne, was kindly provided by Dr. Tim Hoover, USAMRAID, Fort Dietrich, Md. DNA from other B. anthracis strains, such as VNR1-Δ1 and ΔSterne, both plasmid-free; and ΔAmes, pXO2$^+$were prepared in our laboratory following standard procedures for isolation of genomic DNA. The DNA was diluted to a concentration of 1 ng/ml, and the majority of the DNA was in the size range of about 30–50 kbp. DNA from other related bacilli, B. cereus, B. thuringensis, B. subtilis, and Agrobacterium tumifaciens were prepared following similar procedures. The random primers (10-mer) were purchased from commercial sources (University of British Columbia, Vancouver, BC, Canada).

Isolation and Purification of DNA:

DNA from the environmental samples was worked up using a 'Soil DNA Isolation Kit' from MoBio Laboratory, Inc. (CA, USA). Two grams of soil/sludge was processed in three replicates according to the manufacturer's protocol. Approximately 500–1000 ng total DNA was recovered, and much of DNA was ≧3040 kbp in size.

RAPD-PCR Amplification:

Routine PCR reactions were carried out in a final volume of 10 or 20 μl using 96-well tray in GeneAmp PCR System (Perkin Elmer-Cetus). The reaction mix contained 1–30 ng of DNA, 200 μM dNTPs, 2 mM $MgCl_2$, and 0.5 unit of Taq DNA polymerase, and 0.2 μM of selected random decamer (10-mer) primers (Rastogi and Cheng, 1997).

DNA Analysis:

The amplificates following each PCR run were mixed with 6× loading dye in a ratio of 5:1 (DNA:dye). The samples were electrophoresced through 1.4% agarose gel submerged in 1×TAE buffer (Sambrook et al. In: Molecular cloning—A laboratory manual, $2^{nd}$ ed., CSH Lab Press, CSH, NY (1980)) using constant voltage of 100 volts. The DNA in gels was stained with ethidium bromide (0.5 μg/ml) and destained before photographing using Polaroid film 667.

DNA Sequencing:

Automated DNA sequencer model 373 (Perkin Elmer, Applied Biosystems Div., Foster City, Calif.) was used for DNA sequencing. After subcloning of the amplified DNA fragment into pCR-blunt vector (Invitrogen, Carlsbad, Calif.), both strands of cloned DNA fragments were sequenced following manufacturer's protocol. Computer analysis of the DNA was performed with MacVector program (Oxford Molecular Ltd., Oxford, UK).

Quality of DNA from Soil/Sludge:

Soil and sludge contain large number of diverse microorganisms, as well as genetic material released from decaying organisms. Presence of the humus material (humic acids, humates or salts of humic acid, fulvic acids and fulvates, lignite and humin) interferes with detection, measurement, and routine molecular analysis of the DNA (Thurman et al. "Isolation of soil and aquatic humic substances", In: Eds. FH Frimmel and RF Christman, Humic substances and their role in the environment, J Wiley & Sons, Ltd., NY, 1988, 31; Tsai et al, Detection of low numbers of bacterial cells in soils and sediments by polymerase chain reaction, AEM, 58: 754 (1992). DNA isolated using 'MoBio Soil DNA is Kit' was amenable to restriction digestion and ligation (results not shown). These results establish that the commercially available kit is an effective procedure for removal of humus material from environmental DNA.

Example 1

Amplification of Anthrax-specific DNA in Spiked Samples

The inventors herein have identified five random 10-mer primers, designated as 173, 248, 280, 290, and 361, result in amplification of DNA fragments from the chromosomal DNA of wild-type anthrax. These primers did not amplify the similar-sized DNA fragments from the genomic DNA from strains related to anthrax, i.e., *B. cereus, B. thuringiensis*, and an unrelated strain *Agrobacterium tumifaciens* (see FIGS. 2*a* through 3*b*). In addition, genomic DNA from wild-type anthrax and two derivative strains lacking one or both plasmids were used as target DNA. The fact that similar-sized DNA fragments are observed in the three anthrax strains, indicates that the priming sites must be located on the chromosome. The amplification pattern derived from *A. tumifaciens* DNA was very different from *Bacillus* DNA, and therefore, this DNA was not included in subsequent experiments.

As shown in FIG. 4, anthrax-specific fragments were amplified from spiked environmental sludge DNA samples, when primer nos. 173, 248, 280, and 290 were used. The spiked samples included anthrax DNA at a concentration of 0.01 and 0.1 ng and sludge DNA mixed at 10, 50, 100, or 200 ng concentration. In general, presence of 200 ng of sludge DNA resulted in failure of the primers to amplify anthrax-specific DNA fragments. Further, primer no. 280 failed to amplify anthrax-specific DNA fragments even at 50 or less ng of sludge DNA. However, primer nos. 173, 248, and 290 clearly demonstrate the specific ability of these random primers to amplify the anthrax-specific DNA fragments in sludge samples spiked with anthrax DNA.

Example 2

Assessing the Detection Limit

Spiked samples were prepared using 0.001, 0.01, 0.1 or 1 ng of anthrax DNA with 50 ng sludge DNA. These amplification assays were set up in an attempt to determine the detection limit of anthrax DNA in the presence of an overwhelming amount of non-specific background DNA. Typically, in RAPD assays, low stringency annealing conditions are used to allow priming event even if the primers are not fully complementary to the priming sites, i.e., a certain level of mis-match is allowed. In an effort to determine which primers are more specific to the priming sites, an annealing temperature of 52° C. was used to preclude priming events from mismatched sites. As shown in FIG. 5, primer nos. 173 and 280 were able to amplify at high-stringency temperature even in the presence of 0.001 ng (1 pg) control anthrax DNA. This result indicates that the PCR assay is highly sensitive for detection of anthrax DNA even in the presence of 5,000-fold excess of non-specific DNA. Assuming 0.28 pg dry wt./bacterial cell and 3% of the dry wt to be DNA (cited in Neidhardt, FC, ed., In: *Escherichia coli* and Salmonella, cellular and molecular biology, ASM Press (1996)), the ability of a PCR-based technology to detect the presence of 1 pg DNA suggests that this technology would detect DNA from as many, or as few, as 120–150 *B. anthracis* cells. While it is a most desirable objective of the invention to be able to detect the presence of even fewer (preferably 1–10) anthrax cells, no other technology to date has been demonstrated to be as sensitive for anthrax detection as the PCR-based procedures just described.

Example 3

Design and Use of High-Fidelity Primers

High-fidelity forward and reverse primer sets (15–20-bases in length) were designed based on the sequence of the cloned regions. Six sets of primers, F1-B11 (290R), F1-B20 (290F), F2-B12 (280R), F1-B22 (173R), F1-B17 (290F), and F1-B2 (248F) were selected to amplify fragments ranging in length from 144–520 bp. Total DNA isolated from environmental sources, soil and sludge, was spiked with anthrax DNA. Control DNA samples contained 1.65–1.85 ng non-specific DNA and spiked samples contained 1 pg of anthrax DNA. The ratio of non-specific DNA:anthrax DNA was about 1,600:1. As shown in FIG. 6, except for the primer set combination F1-B2, the other five primer sets amplified expected fragments in spiked soil/sludge samples. This result demonstrates that even in the presence of overwhelming non-specific DNA, the designed high-fidelity primers of the invention amplify anthrax-specific fragments.

The principles, preferred embodiments and modes of carrying out the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention. For example, the pairs of primers described are merely representative of a small number of primers that are specifically designed from the five fragments of anthrax chromosomal DNA. Numerous other primer sets and probes derivable from the inventive anthrax chromosomal DNA fragments are within the scope of the protection sought.

What we claim is:

1. An isolated and purified DNA fragment from chromosomal DNA of *B. anthracis* consisting essentially of the nucleotide sequence of SEQ ID NO: 1.

2. An isolated pair of forward and reverse oligonucleotide primers for use in the amplification-based detection of *B. anthracis*, each of said forward and reverse primers consisting of at least 20 to 30 contiguous nucleotides of SEQ ID NO: 1 and optionally including a detectable label, and wherein said forward and reverse primers specifically amplify *B. anthracis* DNA and do not amplify DNA from related strains of *B. cereus, B. thuringienis,* and *B. subtilis,* and wherein said primers do not contain any nucleotides from within the region of nucleotides 441 to 717 of SEQ ID NO:1, inclusive.

3. The forward and reverse primers according to claim 2, wherein said primers do not include said optional detectable label.

4. An isolated oligonucleotide probe for use in hybridization-based detection of *B. anthracis*, said probe consisting of a fragment of at least 30 nucleotides from the nucleotide sequence of SEQ ID NO: 1 which specifically binds complementary strand DNA from *B. anthracis* and does not bind DNA from related strains *B. cereus, B. thuringiensis*, and *B. subtilis*, said probe optionally including a detectable label, and wherein said probe does not contain any nucleotides from within the region of nucleotides 441 to 717 of SEQ ID NO:1, inclusive.

5. The oligonucleotide probe according to claim 4, wherein said probe is bound to a solid support.

6. The oligonucleotide probe according to claim 4, wherein said probe does not include said optional detectable label.

7. A method for detection of *B. anthracis* in an environmental sample containing non-specific DNA, comprising the steps of:
   (a) providing a pair of primers, wherein each of said primers consist of at least 20 to 30 contiguous nucleotides of SEQ ID NO: 1, wherein said pair of primers specifically amplify *B. anthracis* DNA and do not amplify DNA from related strains of *B. cereus, B. thuringienis*, and *B. sibtilis*, wherein said primers optionally include a detectable label, and wherein said primers do not contain any nucleotides from within the region of nucleotides 441 to 717 of SEQ ID NO:1, inclusive;
   (b) mixing said primers with DNA isolated from said environmental sample;
   (c) amplifying any DNA to which the primers in step (b) anneal by use of polymerase chain reaction; and
   (d) detecting any *B. anthracis* DNA in said environmental sample based on the amplification products of step (c).

8. The method of claim 7, wherein said pair of primers do not include said optional detectable label.

9. A method for detection of *B. anthracis* in an environmental sample, comprising the steps of:
   (a) providing at least one oligonucleotide probe, wherein said probe consists of a fragment from the nucleotide sequence of SEQ ID NO: 1 which specifically binds complementary strand DNA from *B. anthracis* and does not bind DNA from related strains *B. cereus, B. thuringiensis*, and *B. subtilis*, said probe optionally including a detectable label, and wherein said probe does not contain any nucleotides from within the region of nucleotides 441 to 717 of SEQ ID NO:1, inclusive;
   (b) conjugating said probe to a solid support;
   (c) contacting said environmental sample with said support-bound probe formed in step
   (b) under conditions favorable for hybridization; and
   (d) detecting any *B. anthracis* DNA in said sample based on the hybridization products of step (c).

10. The method of claim 9, wherein said probe does not include said optional detectable label.

11. A kit for the detection of *B. anthracis*, comprising:
    (a) a carrier to receive therein one or more containers; and
    (b) at least one of said containers including a pair of oligonucleotide primers wherein each of said primers consist of at least 20 to 30 contiguous nucleotides of SEQ ID NO; 1 and wherein said pair of primers specifically amplify *B. anthracis* DNA and do not amplify DNA from related strains of *B. cereus, B. thuringiensis*, and *B. subtilis*, said pair of primers optionally including a detectable label, and wherein said primers do not contain any nucleotides from within the region of nucleotides 441 to 717 of SEQ ID NO:1, inclusive.

12. The kit of claim 11, wherein said pair of primers does not include said optional detectable label.

13. The kit of claim 11, further comprising a second container containing primers for amplifying the TOX gene and the CAP gene of *B. anthracis*.

14. A kit for the detection of *B. anthracis*, comprising:
    (a) a carrier to receive therein one or more containers; and
    (b) at least one of said containers including an isolated oligonucleotide probe, wherein said probe consists of a fragment of at least 30 nucleotides from the nucleotides sequence of SEQ ID NO: 1 and which specifically binds complementary strand DNA form *B. anthracis* and does not bind DNA from related strains *B. cereus, B. thuringiensis*, and *B. subtilis*, said probe optionally including a detectable label, and wherein said probe does not contain any nucleotides from within the region of nucleotides 441 to 717 of SEQ ID NO:1, inclusive.

15. The kit of claim 14, wherein said probe does not include said optional detectable label.

16. The kit of claim 14, further comprising a second container containing primers for amplifying the TOX gene and the CAP gene of *B. anthracis*.

* * * * *

SEQUENCE LISTING

<160> NUMBER OF SEQ ID NOS: 15

<210> SEQ ID NO 1
<211> LENGTH: 985
<212> TYPE: DNA
<213> ORGANISM: Bacillus anthracis

<400> SEQUENCE: 1

```
gcctacgact cactataggg cgaattgggc cctctagatg catgctcgag cggccgccag      60
tgtgatggat atctgcagaa ttcggcttat caagctgctc tactaaatat ggagagctt     120
cgtcagacaa ccttacacct tctgtatatg cttctaattc tgccttcgat tcctcttctg    180
ttaattcact aatttctatt ttgttttccc caaacatatt tggtttatat ggaaaatgat    240
tttgcatcgt caccgcatga ataaatgtag gttgttttct ctttttttaat tcatctatta   300
tttctttact catagataaa tcaccgatat tatctccaac tacttctttg ttttttcatcg   360
tatcttctgc attaaaatta tcgaatccta atgttttata tacatcttcc cgtttataaa    420
acgatcggtt aaaagcatgg attgcacttg cataatatcc ttgtttcttt aattcacttg    480
caactgatgg gatttctttc tgacttggaa tagcttgctg atacggtata gaacctggca    540
ttaaaagact cattgagtaa ctcgttaatg cttcaaattc tgtgtttgct gtattccctc    600
caaatgtagg agctatcgtt tgtcccctg ggaaattctc tgtataacga tgtaaattcg     660
gcactggatc ttcgctaaat gaaagattcg ttagttttgt cggatcccaa gaagcttcac    720
tcataataaa tataatattt ggcttctcta cttttgtttg tgcctttact ttaccgctat    780
attgttttc tatatccttt gcaatttgct gcatatttc ttttgaatat ccctctggct      840
ctttaataac tgtcgtatct aagttactta aaaatccaat aataaaacca ttcgctttat    900
aatttgcagc ttgataagcc gaattccagc acactggcgg ccgttactag ggatccgagc    960
tcggtaccta gcaagggtat caaag                                          985
```

<210> SEQ ID NO 2
<211> LENGTH: 710
<212> TYPE: DNA
<213> ORGANISM: Bacillus anthracis

<400> SEQUENCE: 2

```
ggcgaattgg gccctctaga tgcatgctcg agcggccgcc agtgtgatgg atatctgcag      60
aattcggctt caggcggcgt tggagcaggc tttgtgaaca ttattatgta tgcgattatc     120
gcagtctttta tatctggatt aatggtcgga cggacaccag agttttttagg taagaaaatt    180
gaaggtaagg aaatgaaatt aattgcgta acgatactat ttcatccatt gctcatttta     240
ggatttttcgg cattagctct ttcaacaagt ttagggacgg atgctatttc tcattccggt    300
ttccacggtt taacgcaagt tgtatatgaa tatacatcgt cagctgcgaa taacggatct    360
ggatttgaag gattaggaga taatacaccg ttttggaata ttacgactgg tttagttatg    420
tttttaggac gctacttcag tttaattacg atgctagctg tggcagcttc gctaaaagag    480
aaaacggttg taccagaaac agttggaacg ttccggacag ataatggttt atttggaggc    540
atctttattg ggacgattgt aattgttggt gccgttagca ttcttcccaa tgttagtact    600
cggaccaatt gcagaatttc ttacattgaa gtaatggagg gtaaatgatg agaccggtag    660
tagtaaaaga aaaagagtt aatgagtcac acatacatgc cggtagaaga              710
```

<210> SEQ ID NO 3
<211> LENGTH: 722
<212> TYPE: DNA
<213> ORGANISM: Bacillus anthracis

<400> SEQUENCE: 3

| | | | | | |
|---|---|---|---|---|---|
| gactcctata | gggcgaattg | ggccctctag | atgcatgctc | gagcggccgc | cagtgtgatg | 60 |
| gatatctgca | gaattcggcc | gcgagcactc | tataaagcac | aacaatgggt | tgatactcac | 120 |
| agtccagaag | agattgctga | tgccgtttct | ccgttattta | aagacacttc | aaaagacatt | 180 |
| acagaaaaag | taattgaacg | gtataaaaag | caacattctt | atgcgacaaa | tccgctatta | 240 |
| gatgctgaag | aatggaaaca | gctccaaacg | attatgaaag | aagctggcga | attacaaaaa | 300 |
| gaagttccac | atgaagcgct | cgtcaataca | aaaattgccg | agagcgttat | taagaaatag | 360 |
| aggcgaagtg | tatgagcttt | ttacaaatac | gtaacgtttc | tcactgcttt | ttcgcaaaag | 420 |
| agaatgccaa | gctgattctc | gaaaatatga | gtttacaagt | ggaagaaggc | gaattcattt | 480 |
| ctatacttgg | tccaagtggt | tgcggcaaaa | cgacactcct | ctccattatt | gccgggctgc | 540 |
| ttgatccaat | tgaaggtatc | gtcttttag | atggtgagcc | cattacaacg | aaaacttcat | 600 |
| ctatggggta | tatgttgcag | caaggactac | ttgtttcctt | ggaagacaat | tgaagaaaat | 660 |
| attatgctcg | gacttcatat | ccgaaaaatt | tacgatgaac | agacgaaaga | acatacttta | 720 |
| ca | | | | | | 722 |

<210> SEQ ID NO 4
<211> LENGTH: 754
<212> TYPE: DNA
<213> ORGANISM: Bacillus anthracis

<400> SEQUENCE: 4

| | | | | | |
|---|---|---|---|---|---|
| ctaggtaccg | agctcggatc | cctagtaacg | gccgccagtg | tgctggaatt | cggcttcagg | 60 |
| cggcgtcaca | acaacgatta | agaaaataag | agttaagctc | gttaatactg | tatttaaagc | 120 |
| aatctcattc | ggtgtttttt | gacgagcagc | tccttctact | aacgaaatca | ttttatcaat | 180 |
| aaaggattta | ccaggattac | tcgtaatgac | aatcgtaatc | tcatcactta | caaccatcgt | 240 |
| accgcctgtt | acggaacaaa | aatcaccgcc | cgcttctttt | attacaggtg | ctgattcccc | 300 |
| tgtaatcgca | gattcatcaa | cagacgctaa | tccttaatg | acttcaccat | cacttggaat | 360 |
| catctcacct | tgctttacaa | taacaacgtc | atctttttta | aggtcagttg | ctgaaacttg | 420 |
| aacaatttct | ccatttctt | ttacaacatt | tgcaaacaca | tctttcttcg | actgctttaa | 480 |
| agaatcagct | tgcgctttac | cacgaccttc | tgctaatgct | tctgcaaagt | tcgcaaataa | 540 |
| aactgtaaat | aatagaatga | gagaaacagt | tatattaaac | catcctggta | tactactaga | 600 |
| atgacttgga | agaaacgata | aaatgaacgt | aatgacaaac | ccaatttcta | caacgaacat | 660 |
| aatcggattc | tttatcataa | cttcggatt | caatttcgca | acggattgtt | tcatcgcatg | 720 |
| tttcacgata | tcacgatcca | tcgttttcgc | ttgg | | | 754 |

<210> SEQ ID NO 5
<211> LENGTH: 932
<212> TYPE: DNA
<213> ORGANISM: Bacillus anthracis

<400> SEQUENCE: 5

| | | | | | |
|---|---|---|---|---|---|
| ctacgactcc | tatagggcga | attgggccct | ctagatgcat | gctcgagcgg | ccgccagtgt | 60 |
| gatggatatc | tgcagaattc | ggcttgagta | agcggtatga | taaatgtata | acaactagaa | 120 |

-continued

```
aggagtggta aaacaaaatg tcactagaag cgctcattat ttttctttg ctaaatgcgg      180 gtcagcttgc agagaattcg aaggtggatg tacataaaga gcagaaagat gcttatgtat      240
atgttcagaa agaggaaaat aaataacttt attttatata taaacgaaaa aagccaatcc      300
acaggattgg cttttgtca ttaacgagag tagaactcta cgattaatgc ttcgttgatt      360
tcagctggta actcagcgcg ctcagcatga cgagtgtaag tagcttctaa tttgtcagca      420
tcgaaagtta agtattctgg tacgaagttg ttaacttcga tcgcttcttt aacaacaaca      480
aggttgttag atttttcgcg aacgctgata gtttgaccag gttttacacg gtaagatggg      540
atatctacgc gagcaccatc aaccatgatg tgaccgtggt ttactaattg gcgagctgca      600
cgacgagtgc gagctaagcc catacggtaa actaagttgt caagacgagc ttcaagaagg      660
atcatgaagt tttcgccgtg cttaccaggc attttacctg cttggtcaaa tgtgcgacgg      720
aattgacgct cagtcatgcc gtacatgtga cgaagttttt gtttctcttg taattgtaaa      780
ccgtattctg aaagtttctt acgttggtta ggaccgtgag gacctggtgc gtaagggcgt      840
ttttctaatt cttttcctgt gccgcttact caagccgaat tccagcacac tggcggccgt      900
tactagtgga tccgagctcg gtaccaagca gg                                     932
```

<210> SEQ ID NO 6
<211> LENGTH: 440
<212> TYPE: DNA
<213> ORGANISM: Bacillus anthracis

<400> SEQUENCE: 6

```
gcctacgact cactataggg cgaattgggc cctctagatg catgctcgag cggccgccag      60
tgtgatggat atctgcagaa ttcggcttat caagctgctc tactaaatat tggagagctt     120
cgtcagacaa ccttacacct tctgtatatg cttctaattc tgccttcgat tcctcttctg     180
ttaattcact aatttctatt ttgttttccc caaacatatt tggtttatat ggaaaatgat     240
tttgcatcgt caccgcatga ataaatgtag gttgttttct ctttttttaat tcatctatta     300 tttctttact catagataaa tcaccgatat tatctccaac tacttctttg tttttcatcg     360
tatcttctgc attaaaatta tcgaatccta atgttttata tacatcttcc cgtttataaa     420
acgatcggtt aaaagcatgg                                                  440
```

<210> SEQ ID NO 7
<211> LENGTH: 268
<212> TYPE: DNA
<213> ORGANISM: Bacillus anthracis

<400> SEQUENCE: 7

```
cactcataat aaatataata tttggcttct ctactttgt ttgtgccttt actttaccgc        60
tatattgttt ttctatatcc tttgcaattt gctgcatatt ttcttttgaa tatccctctg      120
gctctttaat aactgtcgta tctaagttac ttaaaaatcc aataataaaa ccattcgctt      180
tataatttgc agcttgataa gccgaattcc agcacactgg cggccgttac tagggatccg      240
agctcggtac ctagcaaggg tatcaaag                                          268
```

<210> SEQ ID NO 8
<211> LENGTH: 22
<212> TYPE: DNA
<213> ORGANISM: Bacillus anthracis

<400> SEQUENCE: 8

```
cattcggtgt ttttgacga gc                                                 22
```

```
<210> SEQ ID NO 9
<211> LENGTH: 24
<212> TYPE: DNA
<213> ORGANISM: Bacillus anthracis

<400> SEQUENCE: 9
ctttgcagaa gcattagcag aagg                                          24

<210> SEQ ID NO 10
<211> LENGTH: 24
<212> TYPE: DNA
<213> ORGANISM: Bacillus anthracis

<400> SEQUENCE: 10
tgttccaaga atgaagcgta ctcc                                          24

<210> SEQ ID NO 11
<211> LENGTH: 22
<212> TYPE: DNA
<213> ORGANISM: Bacillus anthracis

<400> SEQUENCE: 11
tgaagcctac tcccgtttca ag                                            22

<210> SEQ ID NO 12
<211> LENGTH: 22
<212> TYPE: DNA
<213> ORGANISM: Bacillus anthracis

<400> SEQUENCE: 12
tcaccgttag aatcacgcca cc                                            22

<210> SEQ ID NO 13
<211> LENGTH: 22
<212> TYPE: DNA
<213> ORGANISM: Bacillus anthracis

<400> SEQUENCE: 13
gccaaaacat ttatcgtccc ag                                            22

<210> SEQ ID NO 14
<211> LENGTH: 25
<212> TYPE: DNA
<213> ORGANISM: Bacillus anthracis

<400> SEQUENCE: 14
caatgggttg atactcacag tccag                                         25

<210> SEQ ID NO 15
<211> LENGTH: 25
<212> TYPE: DNA
<213> ORGANISM: bacillus anthracis

<400> SEQUENCE: 15
ccttgctgca acatataccc catag                                         25
```